United States Patent
Kilpatrick et al.

(10) Patent No.: US 7,553,292 B2
(45) Date of Patent: Jun. 30, 2009

(54) DEVICE FOR TREATING VULNERABLE PLAQUE

(75) Inventors: Deborah L. Kilpatrick, Los Altos, CA (US); Robert D. Ainsworth, Scotts Valley, CA (US); Murthy V. Simhambhatla, San Jose, CA (US); Jeong S. Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 505 days.

(21) Appl. No.: 11/140,240

(22) Filed: May 26, 2005

(65) Prior Publication Data
US 2005/0222584 A1    Oct. 6, 2005

Related U.S. Application Data

(62) Division of application No. 10/032,322, filed on Dec. 21, 2001, now Pat. No. 6,972,024.

(51) Int. Cl.
*A61M 29/00* (2006.01)
(52) U.S. Cl. ................... 604/103.01; 606/192
(58) Field of Classification Search ......... 606/108, 606/192–198; 604/96.01–103.02, 103.06; 623/1.11
See application file for complete search history.

(56) References Cited

U.S. PATENT DOCUMENTS

| | | | |
|---|---|---|---|
| 5,871,449 A * | 2/1999 | Brown |
| 5,906,636 A * | 5/1999 | Casscells, III et al. |
| 5,924,997 A * | 7/1999 | Campbell |
| 6,203,508 B1 * | 3/2001 | Ren et al. |
| 6,234,996 B1 * | 5/2001 | Bagaoisan |
| 6,245,026 B1 * | 6/2001 | Campbell et al. |
| 6,287,314 B1 * | 9/2001 | Lee et al. |
| 6,344,045 B1 * | 2/2002 | Lim et al. |
| 6,763,260 B2 * | 7/2004 | Kohls |
| 6,790,196 B2 * | 9/2004 | Kokate et al. |

* cited by examiner

*Primary Examiner*—Kevin T Truong
(74) *Attorney, Agent, or Firm*—Fulwider Patton LLP

(57) ABSTRACT

A method of treating vulnerable plaque comprising intentionally damaging or rupturing the vulnerable plaque using a wingless balloon which is inflated from a wingless unexpanded diameter to a limited expanded diameter. This process produces significant increase in ECM synthesis at the site of the damage or rupture. As a result, the method strengthens the vulnerable plaque while minimizing or avoiding damage to the surrounding wall of the body lumen or damaging a stable plaque mistakenly believed to be a vulnerable plaque. The method of the invention is particularly useful in treating a fibroatheroma type of vulnerable plaque. In one embodiment, the balloon is self-limiting such that it expands compliantly at initial inflation pressures, and above nominal pressure it expands noncompliantly. In an alternative embodiment, the balloon is inflated using a diameter-limiting device, such as a device which limits the inflation pressure or the volume of inflation fluid in the balloon.

5 Claims, 2 Drawing Sheets

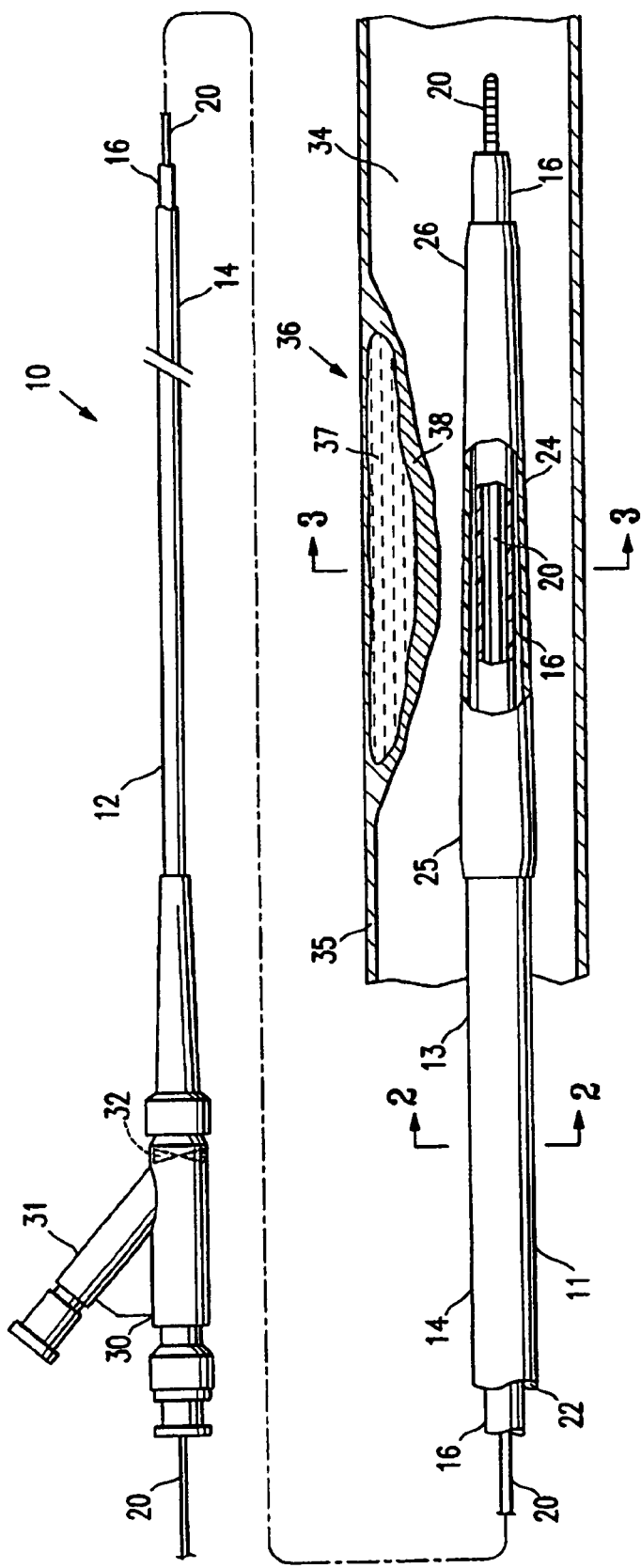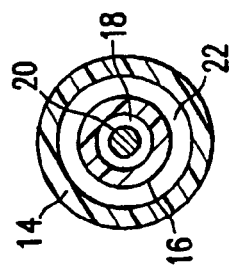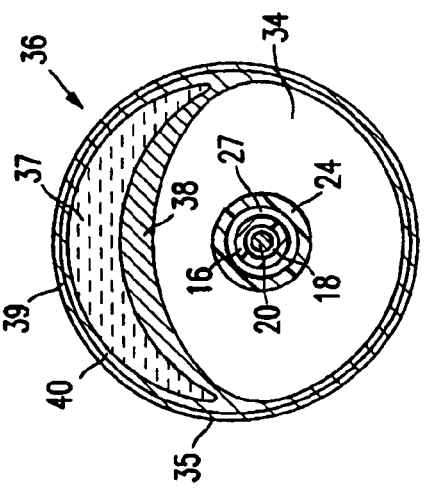

DEVICE FOR TREATING VULNERABLE PLAQUE

This application is a divisional of currently pending U.S. patent application Ser. No. 10/032,322, filed Dec. 21, 2001 now U.S. Pat. No. 6,972,024.

BACKGROUND OF THE INVENTION

This invention generally relates to treatment of atherosclerotic plaque, and particularly to treatment of vulnerable plaque using a balloon catheter.

Percutaneous transluminal coronary angioplasty (PTCA) is a widely used procedure for treating the occlusion of coronary vessels by atherosclerotic plaque. In PTCA procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated vessel and the dilatation catheter can be removed therefrom. In such angioplasty procedures, there may be restenosis of the vessel, i.e. reformation of the arterial blockage from significant neointimal thickening relative to the vessel diameter, which necessitates either another angioplasty procedure, or some other method of repairing or strengthening the dilated area. To reduce the restenosis rate and to strengthen the dilated area, physicians frequently implant a stent inside the artery at the site of the lesion. Studies have shown correlations between vessel damage caused by PTCA and neointimal growth. See Schwartz et al., JACC, Vol. 19, No. 2: 267-74 (1992), incorporated by reference herein in its entirety.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in making catheter balloons. Use of polymeric materials such as polyethyleneterephthalate (PET) that do not stretch appreciably consequently necessitates that the balloon is first formed by blow molding, and then the deflated balloon material, in the form of deflated wings, are folded around the catheter shaft prior to introduction of the balloon into the patient's body lumen. However, it can be desirable to employ balloons that do not have deflated folded wings, but which instead can be expanded to the working diameter within the patient's body lumen from an essentially wingless, cylindrical or tubular shape which conforms to the catheter shaft. For example, catheter balloons have been described which are formed of expanded polytetrafluoroethylene (ePTFE) expanded in place within the patient's body lumen without blow-molding the ePTFE tubing. The ePTFE tubing is formed of a sheet of ePTFE wrapped on a mandrel and then heated to fuse the layers of wrapped material together, and the resulting tubular ePTFE balloon is bonded to a catheter-shaft.

A current therapeutic challenge is the treatment of unstable or vulnerable plaque. The term "vulnerable plaque" refers to an atherosclerotic plaque which may rupture and/or erode, with subsequent thrombosis, typically leading to acute myocardial infarction. In "stable" plaque, the lipid core or necrotic core is protected by a robust fibrous cap composed primarily of long chain extracellular matrix proteins (ECM) such as elastin and collagen. The strength of the fibrous cap is determined largely by ECM density, and especially the density of collagen. Various morphologic features have been associated with vulnerable plaque including thinned or eroded fibrous caps, lesion eccentricity, proximity of constituents having very different structural moduli, e.g., lipid and fibrous tissue, and the consistency and distribution of lipid accumulations. The most common type of vulnerable plaque, often called fibroatheroma, is a raised plaque beneath the innermost arterial layer (i.e., the intima), containing a large lipid core or a large necrotic core rich in lipids, cholesterol crystals, cholesterol esters, macrophages, and other cells, and having a fibrous cap which can become weakened. When ruptured, the luminal blood becomes exposed to highly thrombogenic core material, such as tissue factor (TF), which can result in total thrombotic occlusion of the artery. Due to the substantial danger posed by vulnerable plaque, it would be a significant advance to provide a method of treating such lesions.

SUMMARY OF THE INVENTION

This invention is directed to a method of treating vulnerable plaque, comprising intentionally damaging or rupturing the vulnerable plaque using a wingless balloon which is inflated from a wingless unexpanded diameter to a limited expanded diameter. This process produces significant increase in extracellular matrix protein (ECM) synthesis at the site of the damage or rupture. As a result, the method strengthens the vulnerable plaque while minimizing or avoiding damage to the surrounding wall of the body lumen or to a stable plaque mistakenly believed to be a vulnerable plaque. The method of the invention is particularly useful in treating a fibroatheroma type of vulnerable plaque, although the method is useful in treating any of the types of lesions considered within the class of vulnerable plaque.

The method of the invention generally comprises positioning a wingless balloon of a balloon catheter in a portion of a body lumen having a vulnerable plaque, or having a lesion believed to be a vulnerable plaque, and inflating the wingless balloon. The balloon is inflated from a wingless unexpanded diameter to an expanded diameter into contact with a wall defining the portion of the body lumen having the vulnerable plaque, to thereby intentionally damage or rupture the vulnerable plaque.

The balloon is expanded into contact with the vulnerable plaque to compress the vulnerable plaque. The compression damages or ruptures the fibrous cap of the vulnerable plaque. Damaging the fibrous cap produces some disruption which is not a total cap rupture, such as some form of endothelial denudation, partial fracturing in the cap typically nearest the lumen, and the like. Thus, the term "damage" should be understood to include some form of modification, which induces extracellular matrix synthesis. Rupturing the fibrous cap completely breaks through at least a section of the cap, and thus can allow the entities contained in the lipid or necrotic core of the vulnerable plaque to be released through the cap opening. Consequently, in one embodiment, the method of the invention includes treating the patient with antithrombotic agents during compression of the vulnerable plaque. The damage or rupture to the vulnerable plaque is designed to induce extracellular matrix synthesis and thus increase the extracellular matrix density, thereby increasing the strength of the fibrous cap. The stronger fibrous cap stabilizes the plaque if vulnerable and decreases the risk that a vulnerable plaque will cause thrombotic occlusion.

The term "wingless" should be understood to refer to a balloon which does not have deflated wings folded around the balloon to form a low profile configuration for insertion and advancement of the catheter in the body lumen. Thus, the wingless balloon has little or no wings, unlike catheter balloons which deflate from a blow-molded expanded diameter to form wings. Due to the lack of deflated wings prior to inflation of the balloon in the body lumen, the balloon can be inflated to a working diameter at low pressures to uniformly expand against the vulnerable plaque, and without requiring wings to unfold as the balloon inflates. The wingless balloon expands uniformly to minimize shear loading on the plaque and wall upon inflation, thus preventing or inhibiting dissection in the vessel normal wall opposite the plaque which might otherwise occur.

The wingless balloon may be formed by a variety of conventional methods. For example, in one embodiment, the wingless balloon is formed by heat fusing a wrapped sheet of polymeric material to form a tubular balloon having a wingless unexpanded diameter which is secured to a catheter shaft. Alternatively, depending on the balloon material, the wingless balloon can be formed by heat-shrinking a blow-molded balloon to shrink the balloon to a wingless unexpanded diameter, which is particularly suitable for forming a wingless balloon from a radiation crosslinked polyolefin.

The balloon has a nominal diameter about equal to the inner diameter of the vessel at the site of the vulnerable plaque, so that the balloon is chosen, depending on the diameter of the vulnerable plaque, to expand into contact with the plaque to damage or rupture the plaque without over expanding the vessel. The desired outer diameter of the inflated balloon depends on the size of the body lumen at the vulnerable plaque and the nature of the vulnerable plaque. In a presently preferred embodiment, the outer diameter of the inflated balloon is about 1.5 to about 10 mm, preferably about 2 to about 6 mm, and most specifically, is typically about 2.5 to about 5 mm.

In a presently preferred embodiment, the balloon expands in a self-limiting manner, so that the balloon expands at low pressures to the working diameter and thereafter expands very little. In a presently preferred embodiment, the self-limiting balloon has at least a first layer formed of a polymeric material selected from the group consisting of expanded polytetrafluoroethylene (ePTFE), and ultra high molecular weight polyolefins, which may be an expanded ultrahigh molecular weight polyolefin. A presently preferred ultra high molecular weight polyolefin is ultra high molecular weight polyethylene. The porous ePTFE or ultra high molecular weight polyolefin balloon typically has a second layer of a different material. In one embodiment, the second layer is formed of a material such as a polyurethane elastomer.

Preferably, in the embodiment in which the wingless balloon is a self-limiting balloon (e.g., ePTFE or ultrahigh molecular weight polyolefin balloon), the balloon has a highly compliant radial expansion within a first inflation pressure range, and is noncompliant within a second, higher inflation pressure range. For example, in one embodiment, the self-limiting, wingless balloon has a compliance curve such that the outer diameter increases by about 100% to about 400% of the uninflated diameter at an inflation pressure of up to about 10 atm, and thereafter increases by about 2% to about 15% of nominal at an inflation pressure within a second, higher inflation pressure range of about 10 atm to about 20 atm. Thus, the diameter at a given pressure increases quickly at a first rate up to the nominal diameter at the nominal pressure, and then sharply changes to a second low rate of increase at higher inflation pressures. The nominal pressure required to expand the self-limiting balloon to the nominal diameter, and at which the balloon radial expansion changes from compliant to noncompliant, may range from about 4 atm to about 12 atm, and is typically about 10 atm to about 12 atm, depending on the characteristics of the balloon. In the method of the invention, the self-limiting, wingless balloon is typically inflated at an inflation pressure within the second, higher inflation pressure range, to an expanded diameter at or above the nominal diameter, without expanding the balloon significantly beyond the nominal diameter, to thereby damage or rupture the vulnerable plaque without overexpanding the vessel. Consequently, the balloon expands to produce controlled damage to the vulnerable plaque, in a manner atraumatic to the surrounding tissue and with minimal consequence to a stable plaque.

In another embodiment, the balloon is inflated using a diameter-limiting device, such as a device which limits the inflation pressure or the volume of inflation fluid in the balloon. Pressure-limiting devices include a pressure relief valve in fluid communication with the inflation lumen of the balloon catheter. In a presently preferred embodiment, the pressure relief valve limits the inflation pressure in the balloon to about 4 to about 20, preferably about 4 to about 14 atm, and most preferably to about 4 to about 10 atm. The pressure or volume of the inflation fluid required to inflate the balloon to the desired diameter depends on a variety of factors including the compliance of the balloon, the resistance from the lesion, and the stenosis degree (i.e., extent of occlusion in the lumen). In the embodiment using a diameter-limiting device to inflate the balloon, the balloon can be formed of a variety of suitable materials, such as polyurethane elastomers, polyurethane copolymers such as silicone polyurethanes, segmented polyamide block copolymers, and segmented polyester block copolymers, styrene butadiene rubber or derivatives, and radiation crosslinked polyolefinic elastomers. A balloon formed of these materials typically expands compliantly at the inflation pressures used in the method of the invention, so that the pressure-limiting device results in a low pressure inflation which limits the expanded diameter of the balloon to control the effect on the body lumen from the balloon expansion. For example, in one embodiment, the compliant balloon inflated with a diameter-limiting device expands by about 40% to about 400% of the uninflated diameter at an inflation pressure of about 4 to about 10 atm. Thus, in one embodiment, the pressure-limiting device limits the inflation pressure to about 4 to about 10 atm.

By inflating the wingless balloon using a diameter-limiting device or by using a self-limiting balloon, the method of the invention provides for controlled damage or rupture of the vulnerable plaque and is atraumatic to the healthy wall of the surrounding body lumen. The balloon has an expanded configuration at the working pressure (i.e., the inflation pressure used to expand the balloon into contact with the vulnerable plaque) which is sized such that the balloon does not over expand the healthy wall of the surrounding body lumen. For example, the balloon does not radially over expand or increase in length axially during inflation. Such over expansion of the healthy vessel wall could lead to dissection or occlusion of the body lumen, as for example, by yielding thrombosis or inducing smooth muscle cell neointimal proliferation in the healthy vessel wall. The vulnerable plaque may be eccentrically disposed in the body lumen. In one embodiment, the expanded diameter of the balloon working length is about equal to the inner diameter of body lumen at the location of the vulnerable plaque, so that the inflated balloon does not over expand the healthy vessel wall opposite an eccentric vulnerable plaque In one embodiment, the inflated balloon has a working length which is not longer than the vulnerable plaque, so that the balloon does not expand the healthy vessel wall on either end of the vulnerable plaque. However, in another embodiment, and particularly the embodiment having a self-limiting balloon which inflates to a controlled and limited diameter with increasing pressure, the balloon working length is longer than the vulnerable plaque. In one embodiment, the balloon working length expanded diameter is about equal to or less than the inner diameter of the body lumen located longitudinally adjacent to the vulnerable plaque, so that the expanded balloon may contact but does not over expand the healthy body lumen wall on either end of the vulnerable plaque. Additionally, stable, fibrotic lesions would be minimally affected by the low pressure, limited-diameter dilatation in accordance with the method of the invention. Therefore, treating plaques incorrectly believed to be vulnerable should be a benign process with the method of the invention.

The method of the invention provides for treatment of vulnerable plaque by intentionally damaging or rupturing the vulnerable plaque to thereby produce a stronger fibrous cap around the core of the plaque. Inflating a wingless balloon to a limited expanded diameter damages the vulnerable plaque without damaging the surrounding healthy vessel wall or a stable lesion. The balloon has an initial wingless profile prior to inflation in the body lumen, and inflates to the working diameter at low pressures, preferably with little or no change in compliance behavior with multiple, low pressure inflation-deflation cycles. These and other advantages will become more apparent from the following detailed description and exemplary drawings.

BRIEF DESCRIPTION OF THE DRAWINGS

FIG. 1 is an elevational view, partially in section, of a balloon catheter useful in a method embodying features of the invention, within a body lumen at the site of an eccentric vulnerable plaque.

FIG. 2 is a transverse cross sectional view of the balloon catheter shown in FIG. 1, taken along line 2-2.

FIG. 3 is a transverse cross sectional view of the balloon catheter shown in FIG. 1, taken along line 3-3.

DETAILED DESCRIPTION OF THE INVENTION

Figure 4:
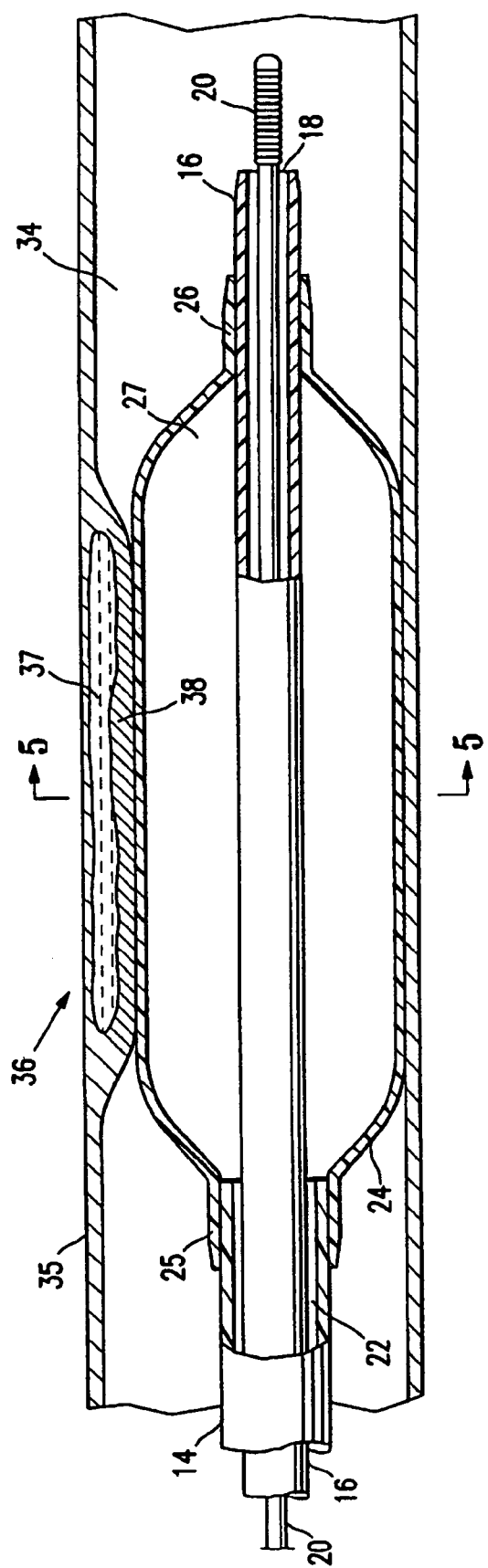
FIG. 4 illustrates the balloon of FIG. 1 inflated at the working pressure to an expanded diameter in contact with the vulnerable plaque.

FIG. 1 illustrates an over-the-wire type balloon catheter 10, such as an angioplasty catheter, useful in a method of treating vulnerable plaque which embodies features of the invention. Catheter 10 generally comprises an elongated catheter shaft 12 having an outer tubular member 14 and an inner tubular member 16. Inner tubular member 16 defines a guidewire lumen 18 (FIG. 2) configured to slidingly receive a guidewire 20. The coaxial relationship between outer tubular member 14 and inner tubular member 16 defines annular inflation lumen 22. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior 27 is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1, the uninflated balloon 24 has a wingless, low profile configuration prior to inflation. FIGS. 2 and 3 illustrate transverse cross sectional views of the distal end of the catheter shown in FIG. 1, taken along lines 2-2 and 3-3, respectively.

In FIG. 1, the balloon 24 is illustrated in a low profile, wingless unexpanded configuration for introduction and advancement within the body lumen 34. Balloon 24 is inflated by introducing inflation fluid into the inflation lumen 22 from arm 31 of proximal adapter 30. In the embodiment of FIG. 1, catheter 10 has a pressure relief valve 32 within the adapter 30, which, in one embodiment, limits the pressure within the balloon to thereby limit the expanded diameter of the inflated balloon 24.

FIG. 1 illustrates the catheter 10 with balloon 24 positioned in a portion of a body lumen 34 defined by a wall 35 having a vulnerable plaque 36. The vulnerable plaque 36 has a lipid or necrotic core 37 surrounded by a thin fibrous cap 38. As best illustrated in FIG. 3, the vessel wall 35 has a medial layer 39 surrounding an intimal layer 40, and vulnerable plaque 36 is within the intimal layer 40. For ease of illustration, medial and intimal layers 39 and. 40 of wall 35 are not separately illustrated in FIG. 1.

Figure 5:
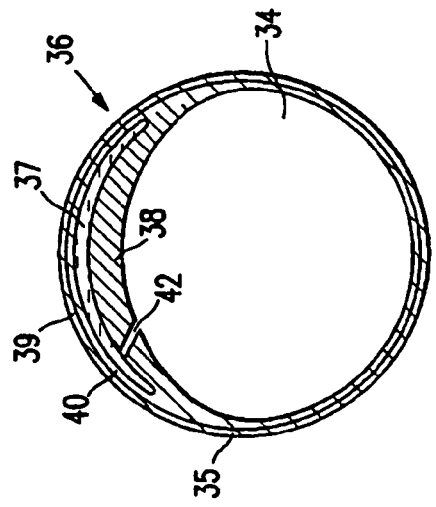
FIG. 5 is a transverse cross sectional view of the inflated balloon expanded into contact with the vulnerable plaque in the body lumen shown in FIG. 4, taken along line 5-5 of FIG. 4.

In accordance with a method of the invention, the balloon 24 is positioned at the site of vulnerable plaque 36 and the balloon 24 is inflated to expand the balloon from a wingless unexpanded diameter to an expanded diameter, to intentionally damage or rupture the vulnerable plaque. The vulnerable plaque can be identified using a variety of methods which have been suggested in the field such as intravascular imaging, spectroscopic measurement, and using temperature sensors to measure the elevated temperature gradients of the vulnerable plaque. It should be understood that the method of the invention is useful in treating lesions believed to be vulnerable plaque, and does not required absolute identification of the plaque as a vulnerable plaque for treatment, and expansion of the balloon in accordance with the method of the invention at the site of stable plaque incorrectly believed to be vulnerable is preferably a benign process. Prior to expanding the balloon to compress the vulnerable plaque, the physician typically determines the diameter of the portion of the body lumen having the vulnerable plaque 36, using conventional imaging methods such as quantitative angiography, ultrasonic or magnetic resonance imaging, or optical coherence tomography (OCT). The physician then chooses the appropriate balloon-to-vessel diameter, and expands the balloon to that preselected diameter which corresponds to the diameter of the portion of the body lumen having the vulnerable plaque 36. FIG. 4 illustrates balloon 24 inflated at the working pressure to an expanded diameter in contact with the portion of the wall 35 having vulnerable plaque 36. The balloon is expanded to a diameter sufficient to compress the vulnerable plaque 36. FIG. 5 illustrates a transverse cross section of the expanded balloon shown in FIG. 4, expanded to compress the vulnerable plaque 36, forming rupture 42. Due to the expansion of the balloon 24 to a controlled, limited diameter, balloon 24 expands into contact with the wall 35 of the body lumen 34 at the site of the vulnerable plaque without damaging the wall 35 adjacent to the vulnerable plaque. Thus, the portions of the wall 35 opposite to and on either end of the eccentric vulnerable plaque 36 of FIG. 1 are not over expanded and damaged by the balloon 24.

Figure 6:
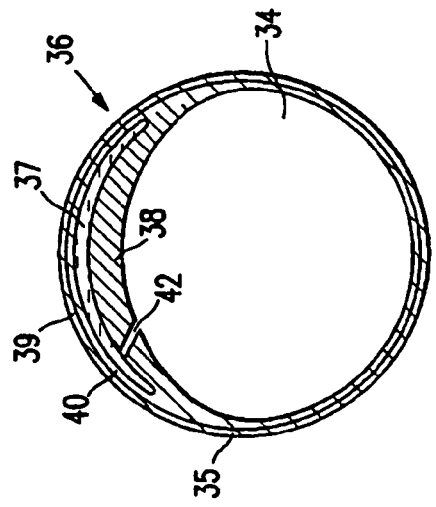
FIG. 6 is a transverse cross sectional view of the vulnerable plaque in the body lumen shown in FIG. 5, after the balloon is deflated and removed from the body lumen.

FIG. 6 illustrates a transverse cross sectional view of the body lumen 34 after the vulnerable plaque 36 is ruptured by the expansion of the balloon 24 illustrated in FIG. 4, directly after deflation of the balloon 24. Antithrombotic agents such as heparin are preferably administered during or before the expansion of balloon 24, so that thrombosis caused by the damage or rupture to the vulnerable plaque 36 is limited or avoided. For example, an antithrombotic agent can be delivered to the body lumen 34 through the guiding catheter (not shown) and/or through the lumen 18 of the inner tubular member 16. Alternatively, an antithrombotic agent can be incorporated in a porous layer (e.g., ePTFE layer) of the balloon 24 and released therefrom when the balloon is inflated. Damaging or rupturing the vulnerable plaque 36 will induce extracellular matrix synthesis to thereby increase the strength of the fibrous cap 38 and reduce the risk of rupture of the plaque 36 in an uncontrolled manner.

In a presently preferred embodiment, balloon 24 is a self-limiting balloon which expands to a limited, controlled diameter. In one embodiment, the self-limiting balloon 24 has at least one layer formed of a porous material such as ePTFE or ultrahigh molecular weight polyethylene. In one embodiment, the ePTFE or ultra high molecular weight polyethylene polymers have a node and fibril microstructure, and are generally not melt extrudable into tubular form. The node and fibril microstructure is produced in the material using conventional methods in which the material is heated, compacted, and stretched. Thus, in one embodiment, the balloon comprises a polymer having a node and fibril microstructure. The ePTFE or ultrahigh molecular weight polyethylene balloon 24 typically has a nonporous second layer. For ease of illustration, multiple layers are not illustrated in balloon 24. In one embodiment, the ePTFE or ultrahigh molecular weight polyethylene balloon 24 has a first layer formed of ePTFE or ultrahigh molecular weight polyethylene, respectively, and a second layer formed of an elastomeric material, including polyurethane elastomers, silicone rubbers, styrene-butadiene-styrene block copolymers, and segmented polyamide block copolymers, and the like. The elastomeric second layer is generally on the interior of balloon, although in other embodiments it may be on the exterior of the balloon. The elastomeric second layer limits or prevents leakage of inflation fluid through the microporous ePTFE or ultrahigh molecular weight polyethylene to allow for inflation of the balloon, and expands elastically to facilitate deflation of the balloon to a low profile deflated configuration. The elastomeric material forming the second layer may consist of a separate layer which neither fills the pores nor disturbs the node and fibril structure of the ePTFE or ultrahigh molecular weight polyethylene first layer, or it may at least partially fill the pores of the first layer. The ePTFE or ultrahigh molecular weight polyethylene layer is typically formed by heat fusing wrapped layers of the material together to form the first layer of the balloon.

Preferably, in the embodiment having a self-limiting balloon, balloon 24 has a high compliance within a first inflation pressure range, and low compliance at higher inflation pressures above the pressure required to reach the nominal diameter of the balloon. For example, self-limiting balloon 24 may expand compliantly within a first inflation pressure range up to about 10 atm, and expand with a low compliance of about 0.01 to about 0.015 mm/atm within the second, higher inflation pressure range of about 10 to about 20 atm, more specifically about 10 to about 14 atm. The pressure ranges of the self-limiting balloon will vary depending on characteristics of the balloon, and the second pressure range, within which the balloon is noncompliant, may be about 4 to about 14 atm, or about 10 to about 20 atm. Although illustrated in the embodiment of FIG. 1, pressure relief valve 32 is typically not used in the embodiment having a self-limiting balloon. In one embodiment, the balloon is inflated within the second pressure range at the site of the vulnerable plaque 36, to an expanded diameter not more than about 2% to about 15% greater than the nominal diameter of the balloon.

In an alternative embodiment, balloon 24 is inflated using a diameter-limiting device, such as pressure relief valve 32. Preferably, the balloon 24 is highly compliant in the embodiment using the pressure relief valve 32. For example, the highly compliant balloon expands to the working expanded diameter at a compliance rate of about 0.04 to about 0.05 mm/atm over the inflation pressure range of about 4 to about 10 atm. Such highly compliant balloon materials include polyurethanes including polyurethane elastomers, silicone styrene elastomers such as C-Flex available from Concept Polymers, styrene butadiene rubber or derivative, segmented polyamide or polyester block copolymers, and radiation crosslinked polyolefinic elastomers. A presently preferred compliant balloon material is a polyurethane elastomer, such as an aromatic polyether polyurethane such as Tecothane 1065D having a Shore durometer hardness of about 65D, available from Themedics. However, a variety of suitable grades of polyurethane can be used including Tecothane 1075D. A balloon formed of polyurethane is preferably formed by melt extruding the polyurethane to form a tubular body which is secured to catheter shaft. The polyurethane tubular body is prestretched or otherwise weakened, as for example by blow molding and heat shrinking, so that the balloon can be expanded in the body lumen from the low profile, wingless diameter.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and wall thickness of 0.004 to 0.008 inch (0.01 to 0.02 cm). The overall length of the catheter 10 may range from about 100 to about 150 cm, and is typically about 135 cm. Preferably, balloon 24 may have a length about 0.5 cm to about 6 cm, and an inflated working diameter of about 3 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations conventionally used in dilatation catheters may be used including a dual lumen extruded shaft having a side-by-side lumens extruded therein. Similarly, although the embodiment illustrated in FIG. 1 is over-the-wire stent delivery catheter, balloons of this invention may also be used with other types of intravascular catheters, such as and rapid exchange dilatation catheters. Rapid exchange catheters generally comprise a distal guidewire port in a distal end of the catheter and a proximal guidewire port distal of the proximal end of the shaft, and typically spaced a substantial distance from the proximal end of the catheter, and a short guidewire lumen extending between the proximal and distal guidewire ports in a distal section of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A device for treating vulnerable plaque, comprising a balloon catheter having a wingless self-limiting balloon with an unexpanded diameter which inflates to a limited, controlled expanded diameter, and the balloon has at least one layer of porous polymeric material with an antithrombotic agent within the pores, and wherein such expanded diameter is selected to intentionally damage such plaque by disrupting a fibrous cap without cap rupture, to thereby strengthen the vulnerable plaque by inducing extracellular matrix protein synthesis.

2. The device of claim 1, wherein said expanded diameter corresponds to the diameter of a portion of body lumen in which the vulnerable plaque is located, whereby the vulnerable plaque can be damaged without damaging the body lumen wall adjacent to the vulnerable plaque.

3. The device of claim 1, wherein the balloon has a highly compliant radial expansion up to a nominal expanded diameter within a first inflation pressure range, and a low compliant radial expansion within a second higher inflation pressure range.

4. The device of claim 3, wherein the porous polymeric material is selected from the group consisting of expanded polytetrafluoroethylene, and expanded ultrahigh molecular weight polyolefin.

5. The device of claim 3, wherein the balloon expands noncompliantly to an expanded diameter of about 2% to about 15% greater than the nominal diameter within the second, higher inflation pressure range.

* * * * *